United States Patent [19]
Fanget et al.

[11] Patent Number: 6,008,036
[45] Date of Patent: Dec. 28, 1999

[54] METHOD FOR PURIFYING VIRUSES BY CHROMATOGRAPHY

[75] Inventors: Bernard Fanget, Saint-Germain-sur-l'Arbresle; Alain Francon, Bessenay, both of France

[73] Assignee: Pasteur Merieux Serums et Vaccins, Lyons, France

[21] Appl. No.: 09/011,503

[22] PCT Filed: Jul. 8, 1996

[86] PCT No.: PCT/FR96/01064

§ 371 Date: May 22, 1998

§ 102(e) Date: May 22, 1998

[87] PCT Pub. No.: WO97/06243

PCT Pub. Date: Feb. 20, 1997

[30] Foreign Application Priority Data

Aug. 10, 1995 [FR] France ................................. 95 09851

[51] Int. Cl.$^6$ .............................. C12N 7/02; A61K 39/12
[52] U.S. Cl. ................. 435/239; 435/235.1; 424/204.1; 424/209.1; 424/224.1
[58] Field of Search ................................ 435/235.1, 239, 435/948; 424/204.1, 211.1, 218.1, 224.1, 209.1

[56] References Cited

U.S. PATENT DOCUMENTS

| | | | |
|---|---|---|---|
| 4,162,192 | 7/1979 | Mizuno et al. | 435/239 |
| 4,525,349 | 6/1985 | Montagnon et al. | 424/89 |
| 4,664,912 | 5/1987 | Wiktor et al. | 424/224.1 |
| 5,837,520 | 11/1998 | Shabram et al. | 435/239 |

FOREIGN PATENT DOCUMENTS

| | | |
|---|---|---|
| 1 441 767 | 5/1966 | France . |
| 95 01797 | 1/1995 | WIPO . |

OTHER PUBLICATIONS

Chemical Abstracts, vol. 51, No. 1, Jan. 10, 1957, Columbus, Ohio, Abstract No. 530f, H.D. Matheka et al, "Ion Exchange For Virus Preparations. I. Influence Of The Ion-Exchange Properties On The Adsorption Of Influenza Virus", XP002000499 & Z. Naturforsch, vol. 11b, 1956, pp. 187–193.

Chemical Abstracts, vol. 51, No. 1, Jan. 10, 1957, Columbus, Ohio, Abstract No. 530g, H.D. Matheka et al, "Ion Exchange For Virus Preparations, II. Fractionation Of Influenza Virus" XP002000500 & Z. Naturforsch., vol. 11b, 1956, pp. 193–199.

*Primary Examiner*—Donna C. Wortman
*Attorney, Agent, or Firm*—Burns, Doane, Swecker & Mathis, L.L.P.

[57] ABSTRACT

A method for purifying viruses from a cell line culture by chromatography, comprising an anion exchange chromatography step followed by a cation exchange chromatography step and optionally a metal-binding affinity chromatography step. The method is particularly suitable for producing viruses for use in vaccines.

15 Claims, No Drawings

METHOD FOR PURIFYING VIRUSES BY CHROMATOGRAPHY

The invention relates to the field of purification of viruses, and more particularly to the purification of viruses obtained by culturing on cell lines.

Harvests of viruses obtained from culturing on cell lines such as Vero cells contain not only the desired viruses but also proteins and DNA originating from the culture cells. However, when the viruses are intended for certain uses, such as the manufacture of vaccines, it is essential for them to be as pure as possible. This is because standards exist which limit, to $100 \cdot 10^{-12}$ g/vaccinal dose, the maximum authorized amount of cellular DNA in vaccines comprising products obtained from continuous and heteroploid cell lines.

Methods for purifying viruses are known in the prior art. Thus, U.S. Pat. No. 4,664,912 discloses in particular a method for purifying rabies virus by zone centrifugation in a sucrose gradient. However, such a method has the drawback of being difficult to automate; in addition, a prior inactivation step is necessary, which may lead to interactions between the virus and the cellular DNA which then make the step for removal of this DNA more difficult.

This reference also discloses a purification method combining a step of gel filtration and a step of ion-exchange chromatography. However, such a purification method does not allow maximum removal of the cellular DNA.

One aim of the invention is thus to propose a novel method for purifying viruses in very high yield which is easy to automate.

Another aim of the invention is to propose a purification method which allows whole, non-degraded viruses to be obtained.

To achieve these aims, the subject of the invention is a method for purifying viruses obtained from a cell line culture, this method consisting in separating by ion-exchange chromatography the viruses from the cell proteins and DNA originating from the culture, characterized in that it comprises at least one step of anion-exchange chromatography and one step of cation-exchange chromatography.

According to a particular characteristic of the method according to the invention, the step of cation-exchange chromatography is carried out after the step of anion-exchange chromatography. Optimized purification yields are thus obtained, compared with inversion of the order of the steps.

According to a particular embodiment, the method according to the invention also comprises a step of affinity chromatography by metal chelation. Thus, the amounts of residual DNA are truly reduced to a minimum.

According to another preferred embodiment, the method according to the invention also consists in carrying out all the chromatography steps at the same pH value. It is thus possible to automate the method easily and to reduce its costs appreciably, while at the same time maintaining its efficiency.

The viruses to be purified according to the method of the invention are viruses obtained by means of cell lines, in particular continuous and heteroploid cell lines, which are thus liable to be combined with cellular DNA. These may be, in particular, rabies virus, Japanese encephalitis virus or influenza virus. These viruses to be purified may have been obtained by culturing on Vero cells on microsupports. This concerns, for example, rabies virus obtained by culturing, as is described in U.S. Pat. No. 4,664,912.

The viral harvest is filtered and then processed, according to the invention, by anion-exchange chromatography and by cation-exchange chromatography.

The anion-exchange chromatography can be an exchange chromatography of weak anions carried out, for example, using gel containing the diethylaminoethyl radical: DEAE Spherodex gel sold by Sepracor, DEAE Sepharose gel sold by Pharmacia, EMD DEAE gel sold by E. Merck. Although this is not common for the removal of nucleic acids, it is preferred to use a strong anion exchanger such as one of the following gels: High Q gel sold by Bio-Rad, Q Sepharose gel sold by Pharmacia, EMD TMAE gel sold by E. Merck.

All of these gels can be used in Tris buffer or in phosphate buffer. Advantageously, a gel is used which allows great availability of the cationic group, as is the case in EMD TMAE from E. Merck, which has chains of 15 to 25 units of the following monomer:

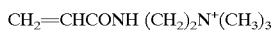

Similarly, according to the method of the invention, the step of cation-exchange chromatography is preferably carried out using a gel which allows great accessibility of the anionic group, as is the case in EMD $SO_3$ sold by E. Merck, which has chains of 15 to 25 units of the following monomer:

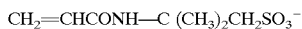

This gel can also be equilibrated using Tris buffer or phosphate buffer.

According to a preferred embodiment of the invention, the anion-exchange chromatography is carried out before the cation-exchange chromatography, the eluate from the first chromatography being, after optional dilution, introduced directly into the second chromatography column. This order of operation allows optimization of the removal of the cellular DNA to be obtained.

The viral suspension obtained by elution of the cation-exchange chromatography column has a degree of purity which is already satisfactory with regard to the standards established for the use of viruses in the manufacture of vaccines.

However, according to a preferred embodiment of the invention, an additional step of affinity chromatography by metal chelation using, for example, the $Ca^{2+}$ ion as metal ion is added to the purification method described above. This chromatography can be carried out using an agarose gel as chelation support, such as the Sepharose® FF chelating gel sold by Pharmacia, which has the following structure:

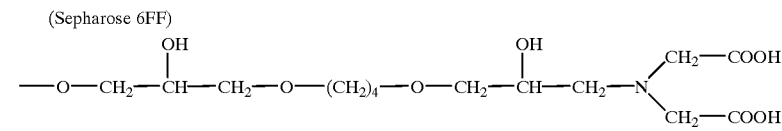

The invention will be better understood on reading the detailed description which follows.

According to the method of the invention, this chelation step is performed in line with the previous two ion-exchange chromatography steps, the eluate from the cation exchanger being introduced directly into the chelation chromatography column.

During this step, the cellular DNA remains bound whereas the virus passes through the gel without being retained.

This additional step makes it possible to bind at least another half of the residual DNA which is, admittedly, already in very low amount but which is, on the other hand, at this stage, very difficult to remove.

The viral suspension thus purified is diluted with a stabilizer and then inactivated according to any known method of the prior art, for example with β-propiolactone, before being concentrated and freeze-dried, so as then to be mixed with the other harvests obtained from the same Vero cell culture and which will constitute the same manufacturing batch.

The vaccines manufactured from such viruses were injected into humans and were well tolerated. In addition, their protective activity in animals was verified by virtue of a test carried out on mice, the results of which were positive.

According to the invention, it is possible, surprisingly and very advantageously, to carry out the entire purification at room temperature in line and always at the same pH, which makes the method simple, easy to automate and reliable; it is especially possible to carry out the entire method under good conditions of sterility.

By virtue of this purification method, whole, non-degraded viruses are obtained whose spicules are visible by electron microscopy, in a very high degree of purity.

EXAMPLE 1

An anion-exchange chromatography column is prepared by introducing EMD TMAE gel sold by E. Merck into a column, through which 1 M sodium hydroxide NaOH is first passed for the purposes of disinfection. The column is then equilibrated with 20 mM Tris buffer at pH 7.5.

A cation-exchange chromatography column is prepared by introducing EMS $SO_3$ gel sold by E. Merck into a column, through which 1 M sodium hydroxide is also passed, followed by 20 mM Tris buffer at pH 7.5.

A metal-chelation affinity chromatography column is prepared by introducing Sepharose® FF chelating gel sold by Pharmacia into a column, through which is passed 1 M sodium hydroxide and then water, followed by loading it with $CaCl_2$ at 3 g/l; the column is then rinsed with water, after which 0.5 M NaCl 20 mM Tris buffer at pH 7.5 is passed through.

EXAMPLE 2

A harvest of rabies virus cultured on Vero cells is filtered using a membrane whose cutoff threshold is 0.65 μm and then on a membrane whose cutoff threshold is 0.45 μm.

This harvest consists of a viral suspension in culture medium also comprising cellular DNA as well as proteins originating both from the Vero cells and from the culture medium. The filtered crude harvest is passed through the anion-exchange chromatography column prepared as described in Example 1. The non-bound part, containing proteins and DNA, is collected at the column outlet for assay purposes. The column is rinsed with 0.1 M NaCl 20 mM Tris buffer at pH 7.5 and the bound viruses are then eluted by passing 0.4 M NaCl 20 mM Tris buffer at pH 7.5 through the column until the characteristic peak for the viruses has passed. The eluate from the first column is diluted to ¼ in line with 20 mM Tris buffer at pH 7.5 and then introduced into the cation-exchange chromatography column prepared according to Example 1.

The non-bound part of this second column is collected for assay purposes. When all of the eluate from the first column containing the virus has passed through the second column, it is rinsed with 0.1 M NaCl 20 mM Tris buffer at pH 7.5 and the bound viruses are then eluted by passing 0.5 M NaCl 20 mM Tris buffer through until the characteristic peak for the viruses has passed.

The eluate from this second column is introduced directly, without dilution, into the metal-chelation affinity chromatography column prepared according to Example 1. This time, the DNA complexes with the $Ca^{++}$ ions present in the column, whereas the virus passes through the column and is collected at the outlet in order to be combined with a stabilizer and inactivated. The DNA complexed with the $Ca^{++}$ ions is eluted by passing 50 mM EDTA solution through the column.

The ion-exchange chromatography columns are regenerated by passing 1 M NaCl 20 mM Tris buffer at pH 7.5 through and are disinfected with 1 M sodium hydroxide before being used for the purification of the other harvests originating from the same culture, which will all be pooled to constitute a single manufacturing batch.

EXAMPLE 3

The amounts of purified cellular proteins and DNA are assayed for each harvest, after each chromatography step.

The total proteins are assayed by means of the Lowry method and the total DNA is assayed using the Threshold machine from Molecular Device.

The results obtained, taking an average of the yields per step for each culture harvest, expressed as a residual percentage for each of the steps of the purification method, are as follows:

| Yield (%) | Total DNA | Total proteins |
|---|---|---|
| Anion-exchange column | 0.02 | 0.056 |
| Cation-exchange column | 27 | 25 |
| Metal-chelation affinity column | 80 | |

Overall, by means of the purification according to the invention, only 0.004% of the cellular DNA and 1.4% of the proteins present in the crude harvests remain.

The purification carried out is thus entirely satisfactory.

The infectivity of the viruses obtained is also verified at each step, by means of measuring their infectious titre in $CCID_{50}$ and observation by electron microscope. It is observed that the integrity of the viruses is well conserved throughout the method.

When the viruses thus produced are used in the manufacture of vaccines against rabies, it is possible to prepare doses containing not more than 30 to $40 \cdot 10^{-12}$ g of cellular DNA per dose, which is a considerably smaller amount than the standard of $100 \cdot 10^{-12}$ g.

We claim:

1. A method for purifying viruses obtained from a cell culture by ion exchange chromatography comprising
   introducing the viruses in cell culture medium onto a first chromatography exchanger,
   eluting the viruses of interest from the first chromatography exchanger,
   introducing the resulting eluate into a second chromatography exchanger, and eluting the viruses of interest from the second chromatography exchanger;

wherein one of said first chromatography exchanger and said second chromatography exchanger is an anion exchanger and the other is a cation exchanger.

2. The method according to claim 1, wherein the anion exchanger is a strong anion exchanger.

3. The method according to claim 1, wherein the cation exchanger comprises EMD $SO_3$.

4. The method according to claim 1, wherein cation exchange is carried out after anion exchange.

5. The method according claim 1, further comprising a step of affinity chromatography by metal chelation.

6. The method according to claim 5, wherein the metal chelation is carried out using calcium ions.

7. The method according to claim 1, wherein the viruses to be purified are obtained by culturing on continuous and heteroploid cell lines.

8. The method according to claim 1, wherein the viruses to be purified are obtained by culturing on Vero cells.

9. The method according to claim 1, wherein the viruses to be purified are rabies viruses.

10. The method according to claim 1, wherein the viruses to be purified are Japanese encephalitis viruses.

11. The method according to claim 1, wherein the viruses to be purified are influenza viruses.

12. The method according to claim 1, comprising carrying out all of the chromatography steps at the same pH value.

13. The method according to claim 1, wherein said method is an in-line method.

14. A method according to claim 1, which is carried out at room temperature.

15. A method according to claim 1, which is carried out under sterile conditions.

* * * * *